United States Patent
Yang et al.

(10) Patent No.: US 12,193,846 B2
(45) Date of Patent: Jan. 14, 2025

(54) AMBIENT LIGHT CANCELLATION CIRCUIT

(71) Applicant: REALTEK SEMICONDUCTOR CORPORATION, Hsinchu (TW)

(72) Inventors: Tzu-Hsuan Yang, Hsinchu (TW); Ming-Chih Kuan, Hsinchu (TW)

(73) Assignee: REALTEK SEMICONDUCTOR CORPORATION, Hsinchu (TW)

( * ) Notice: Subject to any disclaimer, the term of this patent is extended or adjusted under 35 U.S.C. 154(b) by 110 days.

(21) Appl. No.: 18/196,465

(22) Filed: May 12, 2023

(65) Prior Publication Data

US 2023/0363716 A1  Nov. 16, 2023

Related U.S. Application Data

(60) Provisional application No. 63/342,592, filed on May 16, 2022.

(30) Foreign Application Priority Data

Aug. 4, 2022  (TW) .................................. 111129390

(51) Int. Cl.
*A61B 5/00* (2006.01)
*A61B 5/024* (2006.01)

(52) U.S. Cl.
CPC ........ *A61B 5/7203* (2013.01); *A61B 5/02416* (2013.01); *A61B 5/7225* (2013.01)

(58) Field of Classification Search
CPC .. A61B 5/7203; A61B 5/02416; A61B 5/7225
See application file for complete search history.

(56) References Cited

U.S. PATENT DOCUMENTS

2014/0061472 A1* 3/2014 Salvestrini ............. H04N 25/77
250/339.02

OTHER PUBLICATIONS

M. Konijnenburg et al., "A multi (bio) sensor acquisition system with integrated processor power management 8x8 LED drivers and simultaneously synchronized ECG BIO-Z GSR and two PPG readouts", IEEE J. Solid-State Circuits, vol. 51, No. 11, pp. 2584-2595, Nov. 2016.

* cited by examiner

*Primary Examiner* — Georgia Y Epps
*Assistant Examiner* — Don J Williams
(74) *Attorney, Agent, or Firm* — WPAT, PC

(57) ABSTRACT

An ambient light cancellation circuit functions as a $K^{th}$-order filter to filter out an ambient light signal of the detection signal, wherein the K is not fewer than two. The circuit includes a capacitive transimpedance amplifying circuit including an amplifier, a capacitor circuit, and a switch circuit. The capacitor circuit includes one or more capacitive paths coupled in parallel. The switch circuit couples the amplifier with the capacitor circuit in a non-cross manner or a cross manner. The non-cross manner is applied N times to let the capacitor circuit sample the detection signal N times while the detection signal includes a controllable-light signal and the ambient light signal; and the cross manner is applied M times to let the capacitor circuit sample the inversion of the detection signal M times while the detection signal includes the ambient light signal without the controllable-light signal, wherein (N+M) equals (K+1).

19 Claims, 10 Drawing Sheets

AMBIENT LIGHT CANCELLATION CIRCUIT

BACKGROUND OF THE INVENTION

1. Field of the Invention

The present disclosure relates to an ambient light cancellation circuit, especially to an ambient light cancellation circuit functioning as a $K^{th}$-order filter for filtering out an ambient light signal.

2. Description of Related Art

A general photoplethysmography (PPG) device illuminates skin with a controllable light source (e.g., a light emitting diode (LED)) and detects the reflection light to measure the variation in optical absorption and thereby realize multiple kinds of applications (e.g., the measurement of heartbeat and blood oxygen). However, in addition to the controllable light source, other light sources (e.g., sunlight and indoor light) usually exist in the same space, and the influence of these light sources (hereinafter referred to as "ambient light") should be eliminated to ensure the accuracy of the measurement of the variation in optical absorption. A hardware circuit can be used to cancel the ambient light; however, using a hardware circuit functioning as a multi-order filter to cancel the ambient light is not found in the existing ambient-light cancellation technologies.

SUMMARY OF THE INVENTION

An object of the present disclosure is to provide an ambient light cancellation circuit functioning as a multi-order filter for cancelling an ambient light signal.

A first embodiment of the ambient light cancellation circuit of the present disclosure functions as a $K^{th}$-order filter to sample a detection signal (K+1) times during a sampling period and thereby filter out an ambient-light signal of the detection signal, wherein the K is an integer greater than one and the detection signal is generated by a photoelectric device. This embodiment includes a capacitive transimpedance amplifying circuit including an amplifier, a capacitor circuit, and a switch circuit. The amplifier includes an input node, an inverting input node, and an output node, wherein the input node is for receiving a reference voltage and the inverting input node is for receiving the detection signal. The capacitor circuit includes: a first capacitive path including a first capacitor which includes a first electrode and a second electrode. The switch circuit includes a first switch, a second switch, a third switch, and a fourth switch. The first switch is set between the first electrode and the inverting input node; the second switch is set between the second electrode and the output node; and the first switch and the second switch are scheduled to be turned on during N time slot(s) and to be turned off during M time slot(s) so as to couple the first electrode with the inverting input node and couple the second electrode with the output node during the N time slot(s) and thereby allow the first capacitor to sample the detection signal during the N time slot(s), wherein the N time slot(s) and the M time slot(s) are included in the sampling period, each of the N and the M is a positive integer, and the sum of the N and the M is not greater than (K+1). The third switch is set between the second electrode and the inverting input node; the fourth switch is set between the first electrode and the output node; and the third switch and the fourth switch are scheduled to be turned on during the M time slot(s) and to be turned off during the N time slot(s) so as to couple the second electrode with the inverting input node and couple the first electrode with the output node during the M time slot(s) and thereby allow the first capacitor to sample the inversion of the detection signal during the M time slot(s). The detection signal includes a controllable-light signal and the ambient-light signal during I time slot(s); the detection signal includes the ambient-light signal without including the controllable-light signal during J time slot(s); the I time slot(s) is/are the N time slot(s) or the M time slot(s). When the I time slot(s) is/are the N time slot(s), the J time slot(s) is/are the M time slot(s); and when the I time slot(s) is/are the M time slot(s), the J time slot(s) is/are the N time slot(s).

In an exemplary implementation of the first embodiment, the capacitor circuit includes a plurality of capacitive paths coupled in parallel. The plurality of capacitive paths include the aforementioned first capacitive path, and the conducting states of the multiple capacitive paths and the capacitances of the multiple capacitive paths jointly determine a plurality of filter coefficients of the $K^{th}$-order filter.

A second embodiment of the ambient light cancellation circuit of the present disclosure functions as a $K^{th}$-order filter to sample a detection signal (K+1) times during a sampling period and thereby filter out an ambient-light signal of the detection signal, wherein the K is an integer and the detection signal is generated by a photoelectric device. This embodiment includes a capacitive transimpedance amplifying circuit including an amplifier, a capacitor circuit, and a switch circuit. The amplifier includes an input node, an inverting input node, and an output node, wherein the input node is for receiving a reference voltage and the inverting input node is for receiving the detection signal. The capacitor circuit includes a first capacitive path and a second capacitive path. The first capacitive path includes a first capacitor which includes a first electrode and a second electrode; and the second capacitive path is coupled with the first capacitive path in parallel, and includes a second capacitive-path switch and a second capacitor which includes a third electrode and a fourth electrode, wherein one end of the second capacitive-path switch is coupled with the third electrode and the other end of the second capacitive-path switch is coupled with the first electrode. The switch circuit includes a first switch, a second switch, a third switch, and a fourth switch. The first switch has one end coupled with both of the first electrode and the second capacitive-path switch and has another end coupled with the inverting input node; and the second switch has one end coupled with both of the second electrode and the fourth electrode and has another end coupled with the output node, wherein the first switch and the second switch are scheduled to be turned on during N time slot(s) and to be turned off during M time slot(s) so as to couple the first electrode with the inverting input node and couple the second electrode with the output node during the N time slot(s) and thereby allow the first capacitor to sample the detection signal during the N time slot(s), the N time slot(s) and the M time slot(s) are included in the sampling period, each of the N and the M is a positive integer, and the sum of the N and the M is not greater than (K+1). The third switch has one end coupled with both of the second electrode and the fourth electrode and has another end coupled with the inverting input node; and the fourth switch has one end coupled with both of the first electrode and the second capacitive-path switch and has another end coupled with the output node, wherein the third switch and the fourth switch are scheduled to be turned on during the M time slot(s) and to be turned off during the N time slot(s) so as to couple the second electrode with the inverting input node and couple the first electrode with the output node during the M time slot(s) and thereby allow the first capacitor to sample the inversion of the detection signal during the M time slot(s). In the above embodiment, the second capacitive-path switch is only turned on during X time slot(s) which as a whole is a part of the whole of the N time slot(s) and the M time slot(s), the X time slot(s) can be the N time slot(s) or be different from the N time slot(s), and the X is a positive integer. Furthermore, the detection signal includes a controllable-light signal and the ambient-light signal during I time slot(s); the detection signal includes the ambient-light signal without including the controllable-light signal during J time slot(s); the I time slot(s) is/are the N time slot(s) or the M time slot(s); when the I time slot(s) is/are the N time slot(s), the J time slot(s) is/are the M time slot(s); and when the I time slot(s) is/are the M time slot(s), the J time slot(s) is/are the N time slot(s).

A modification to the second embodiment includes the following changes: the second capacitive-path switch is set at the other side of the second capacitor, and thus one end of the second capacitive-path switch is coupled with the fourth electrode and the other end of the second capacitive-path switch is coupled with the second electrode.

These and other objectives of the present invention will no doubt become obvious to those of ordinary skill in the art after reading the following detailed description of the preferred embodiments that are illustrated in the various figures and drawings.

DETAILED DESCRIPTION OF THE PREFERRED EMBODIMENTS

The present specification discloses an ambient light cancellation circuit functioning as a multi-order filter for filtering out an ambient light signal. The ambient light cancellation circuit is applicable to a Photoplethysmography (PPG) device, but the application of the present invention is not limited thereto.

Figure 1:
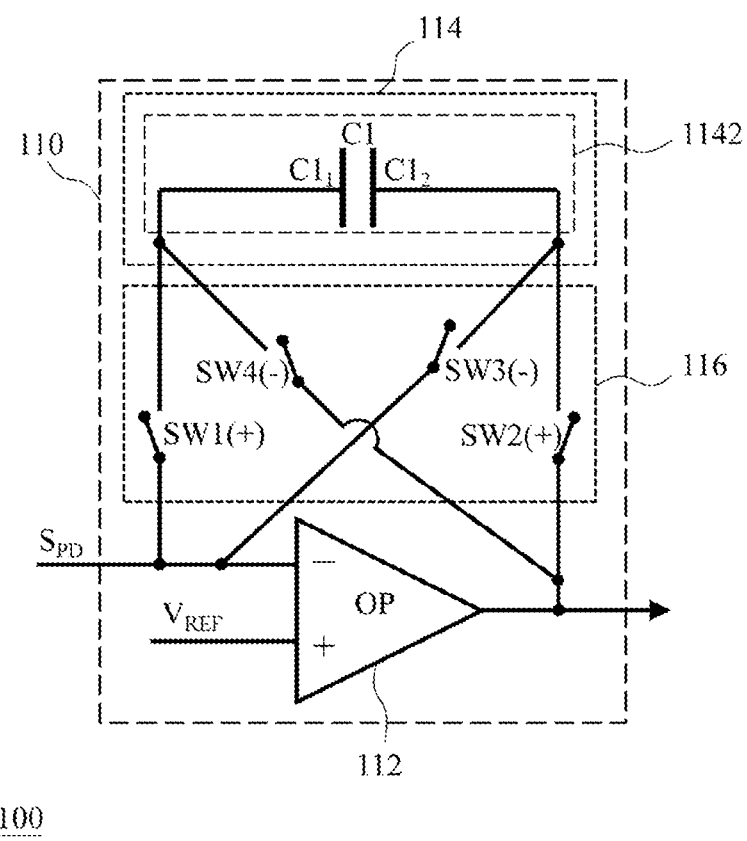
FIG. 1 shows an embodiment of the ambient light cancellation circuit of the present disclosure.

FIG. 1 shows an embodiment of the ambient light cancellation circuit of the present disclosure. The ambient light cancellation circuit 100 of FIG. 1 functions as a $K^{th}$-order filter to sample a detection signal $S_{PD}$ (K+1) times during a sampling period and thereby filter out an ambient-light signal of the detection signal $S_{PD}$, wherein the K is a positive integer (e.g., an integer greater than one) and the detection signal $S_{PD}$ is generated by a photoelectric device (e.g., a photo diode (PD)).

Referring to FIG. 1, the ambient light cancellation circuit 100 includes a capacitive transimpedance amplifying circuit 110. The capacitive transimpedance amplifying circuit 110 includes an amplifier 112, a capacitor circuit 114, and a switch circuit 116. The details of these circuits are described in the following paragraphs.

Referring to FIG. 1, the amplifier 112 includes an input node (i.e., the symbol "+" of the amplifier 112), an inverting input node (i.e., the symbol "−" of the amplifier 112), and an output node. The input node is for receiving a reference voltage $V_{REF}$ and the inverting input node is for receiving the detection signal $S_{PD}$, wherein the reference voltage $V_{REF}$ can be determined according to the demand for implementation.

Referring to FIG. 1, the capacitor circuit 114 includes a first capacitive path 1142. The first capacitive path 1142 includes a first capacitor C1. The first capacitor C1 includes a first electrode $C1_1$ and a second electrode $C1_2$.

Referring to FIG. 1, the switch circuit 116 includes a first switch SW1(+), a second switch SW2(+), a third switch SW3(−), and a fourth switch SW4(−). The first switch SW1(+) is set between the first electrode $C1_1$ and the inverting input node; the second switch SW2(+) is set between the second electrode $C1_2$ and the output node; the third switch SW3(−) is set between the second electrode $C1_2$ and the inverting input node; and the fourth switch SW4(−) is set between the first electrode $C1_1$ and the output node. The first switch SW1(+) and the second switch SW2(+) are scheduled to be turned on during N time slot(s) and to be turned off during M time slot(s) so as to couple the first electrode $C1_1$ with the inverting input node and couple the second electrode $C1_2$ with the output node during the N time slot(s) and thereby allow the first capacitor C1 to sample the detection signal $S_{PD}$ during the N time slot(s). The N time slot(s) and the M time slot(s) are included in the aforementioned sampling period, each of the N and the M is a positive integer, and the sum of the N and the M is not greater than (K+1) (e.g., (N+M)=(K+1)). The third switch SW3(−) and the fourth switch SW4(−) are scheduled to be turned on during the M time slot(s) and to be turned off during the N time slot(s) so as to couple the second electrode $C1_2$ with the inverting input node and couple the first electrode $C1_1$ with the output node during the M time slot(s) and thereby allow the first capacitor C1 to sample the inversion of the detection signal $S_{PD}$ during the M time slot(s). It is noted that the definition of the detection signal $S_{PD}$ and the definition of the inversion of the detection signal $S_{PD}$ are corresponding definitions, and thus are interchangeable.

Referring to FIG. 1, the detection signal $S_{PD}$ includes a controllable-light signal (e.g., a light signal originated from an LED) and the ambient-light signal during I time slot(s); the detection signal $S_{PD}$ includes the ambient-light signal without including the controllable-light signal during J time slot(s); the I time slot(s) can be the N time slot(s) or the M time slot(s). When the I time slot(s) is/are the N time slot(s), the J time slot(s) is/are the M time slot(s); and when the I time slot(s) is/are the M time slot(s), the J time slot(s) is/are the N time slot(s). For example, the ambient light cancellation circuit 100 is applied to a PPG device, the controllable-light signal is originated from at least one controllable light source (e.g., at least one LED) of the PPG device, the at least one controllable light source is turned on to emit light during the N time slot(s), and is turned off to stop emitting light during the M time slot(s), and the ambient light signal varies with the variation in the intensity of the ambient light in the same space during the (N+M) time slots; on the basis of the above: the switch circuit 116 couples the amplifier 112 with the capacitor circuit 114 in a non-cross manner during the N time slot(s) to allow the capacitor circuit 114 to sample the detection signal $S_{PD}$ and generate N mixed-light sampling result(s); the switch circuit 116 couples the amplifier 112 with the capacitor circuit 114 in a cross manner during the M time slot(s) to allow the capacitor circuit 114 to sample the inversion of the detection signal $S_{PD}$ and generate M ambient-light sampling result(s); and the (N+M) sampling results are related with the variation in the charges stored in the capacitor circuit 114 and can be learned from the variation in the voltage at the output node of the amplifier 112. It is noted that the control over the switch circuit 116 can be realized with known/self-developed technologies. It is also noted that the control over the switch circuit 116 is corresponding to the control over the aforementioned at least one controllable light source. The control over the at least one controllable light source falls beyond the scope of the present disclosure.

Figure 2:
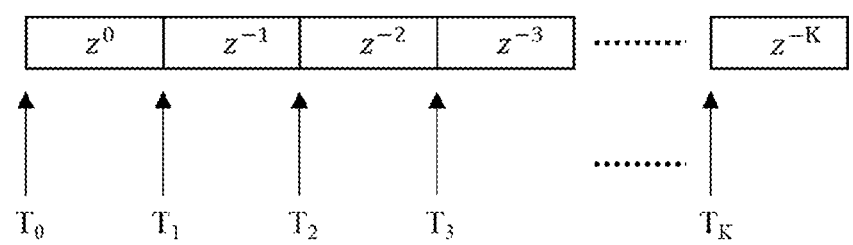
FIG. 2 shows the capacitive transimpedance amplifying circuit of FIG. 1 performing Z-domain sampling in time domain.

Referring to FIG. 1, the switch circuit 116 controls the coupling between the amplifier 112 and the capacitor circuit 114 to make the capacitive transimpedance amplifying circuit 110 perform time domain sampling as in Z-domain (i.e., Z-transform) as shown in FIG. 2 and obtain the aforementioned N mixed-light sampling result(s) and the M ambient-light sampling result(s), wherein the Z-domain sampling and the time domain are known in this technical field. Providing (M+N)=(K+1), the $K^{th}$-order filter (i.e., the ambient light cancellation circuit 100) is characterized by the conversion equation "$c_0 z^0 + c_1 z^{-1} + c_2 z^{-2} + \ldots + c_K z^{-K}$". Regarding the above equation, $c_0 \sim c_K$ are filter coefficients of the $K^{th}$-order filter and can be determined and/or adjusted according to the demand for implementation, and $z^0 \sim z^{-K}$ are (K+1) sampling results (i.e., the N mixed-light sampling result(s) and the M ambient-light sampling result(s)) obtained in sampling time sequence (i.e., the sequence of $T_0, T_1, T_2, T_3, \ldots,$ and $T_K$ in FIG. 2). For example, if (M+N)=(K+1) and N=M=2, the $K^{th}$-order filter is a third-order filter; when the (M+N) sampling results are "a mixed-light sampling result obtained at $T_0$, an ambient-light sampling result obtained at $T_1$, an ambient-light sampling result obtained at $T_2$, and a mixed-light sampling result obtained at $T_3$" in sequence, the conversion equation of the third-order filter can be expressed as "$1z^0 - z^1 - z^{-2} + z^{-3}$", which means the filtration result of the third-order filter is the sum of $z^0, -z^{-1}, -z^{-2},$ and $z^{-3}$. In the above example, after obtaining the four sampling results $z^0, -z^{-1}, -z^{-2},$ and $z^{-3}$, the third-order filter outputs the sum of the sampling results (i.e., the sum of $z^0, -z^{-1}, -z^{-2},$ and $z^{-3}$) to a back-end circuit (e.g., an analog-to-digital converter).

Figure 3A:
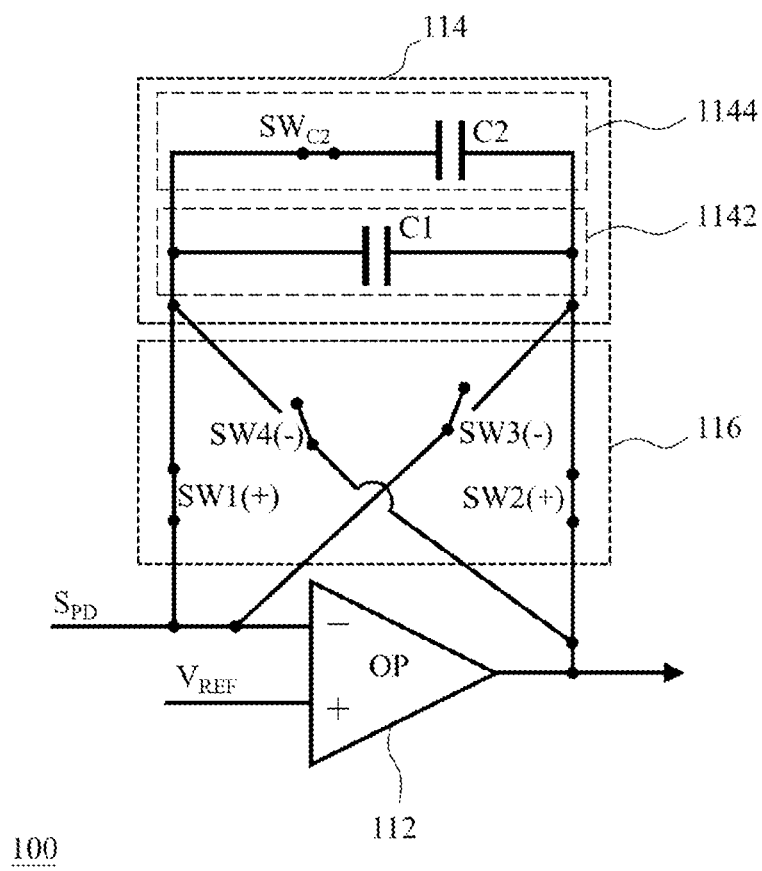
FIGS. 3a~3b jointly shows an exemplary implementation of the ambient light cancellation circuit of the present disclosure.
Figure 3B:
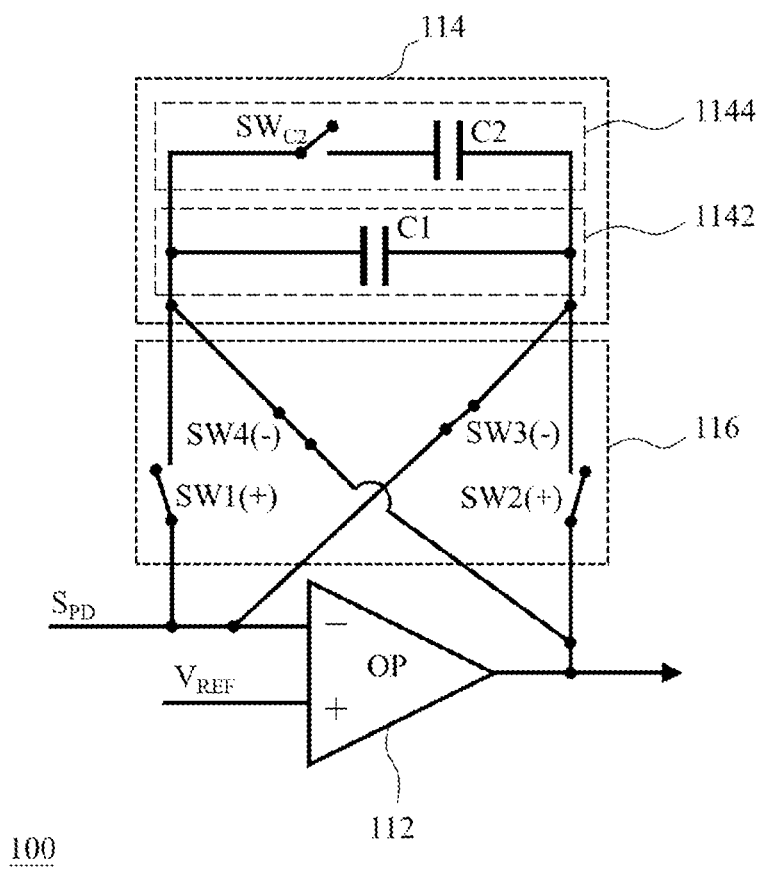

The filter coefficients $c_0 \sim c_K$ of the conversion equation "$c_0 z^0 + c_1 z^{-1} + c_2 z^{-2} + \ldots + c_K z^{-K}$" can be determined and/or dynamically adjusted according to the demand for implementation. For example, as shown in FIGS. 3a~3b, the capacitor circuit 114 further includes a second capacitive path 1144. The second capacitive path 1144 is coupled with the first capacitive path 1142 in parallel, and includes a second capacitive-path switch $SW_{C2}$ and a second capacitor C2. In FIGS. 3a-3b, the capacitance of the second capacitor C2 is equal to the capacitance of the first capacitor C1, and each of the two capacitances is $$\frac{C}{2};$$

accordingly, the equivalent capacitance of the parallel-connected capacitors C1 and C2 is $$\frac{C}{2} + \frac{C}{2} = C.$$

Referring to FIG. 2 and FIG. 3a, during the even time slots $T_0$ and $T_2$, the switch circuit 116 couples the amplifier 112 with the capacitor 114 in a non-cross manner while the second capacitive-path switch $SW_{C2}$ is turned on, and thus the first capacitive path 1142 and the second capacitive path 1144 sample the detection signal $S_{PD}$ simultaneously (i.e., both the first capacitor C1 and the second capacitor C2 are charged/discharged); providing the charge/discharge amount in a unit of time $\Delta T$ is $Q_1$, the voltage difference between the inverting input node and the output node of the amplifier 112 is $$V_1 = \frac{Q_1}{C}.$$

Referring to FIG. 2 and FIG. 3b, during the odd time slot T1, the switch circuit 116 couples the amplifier 112 with the capacitor 114 in a cross manner while the second capacitive-path switch $SW_{C2}$ is turned off, and thus the first capacitive path 1142 samples the inversion of the detection signal $S_{PD}$ (i.e., only the first capacitor C1 is discharged/charged); providing the discharge/charge amount in the unit of time $\Delta T$ is $Q_2$, the voltage difference between the inverting input node and the output node of the amplifier 112 is $$V_2 = -\frac{Q_2}{\frac{C}{2}} = -\frac{2Q_2}{C};$$

as a result, if $Q_2 \approx Q_1$, $V_2 \approx -2V_1$. In light of the above, the ambient-light cancellation 100 functions as a second-order filter and generates a filtration result "$1z^0 - 2z^{-1} + z^{-2}$" which can be scaled up/down with a known/self-developed analog/digital manner. It is noted that the K is a positive integer in the example of FIGS. 3a~'3b.

Figure 4A:
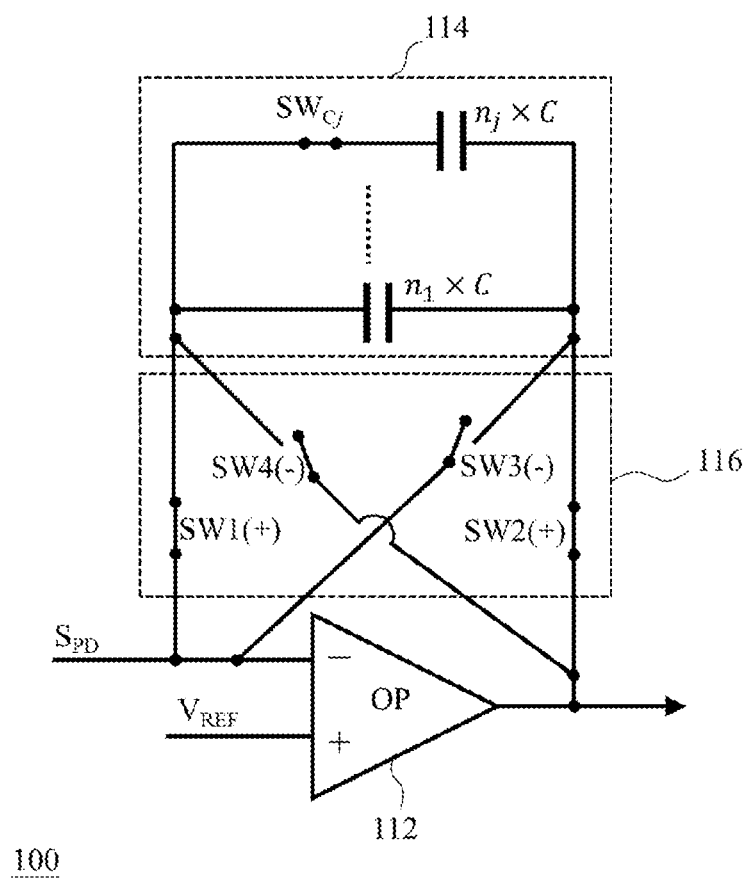
FIGS. 4a~4c jointly shows an exemplary implementation of the ambient light cancellation circuit of the present disclosure.
Figure 4B:
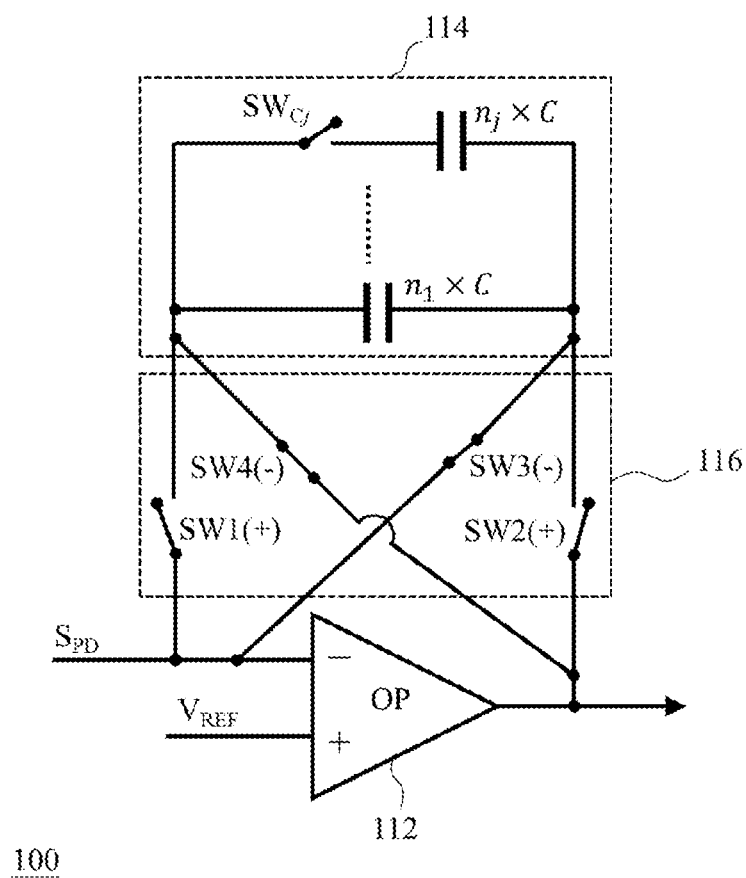
Figure 4C:
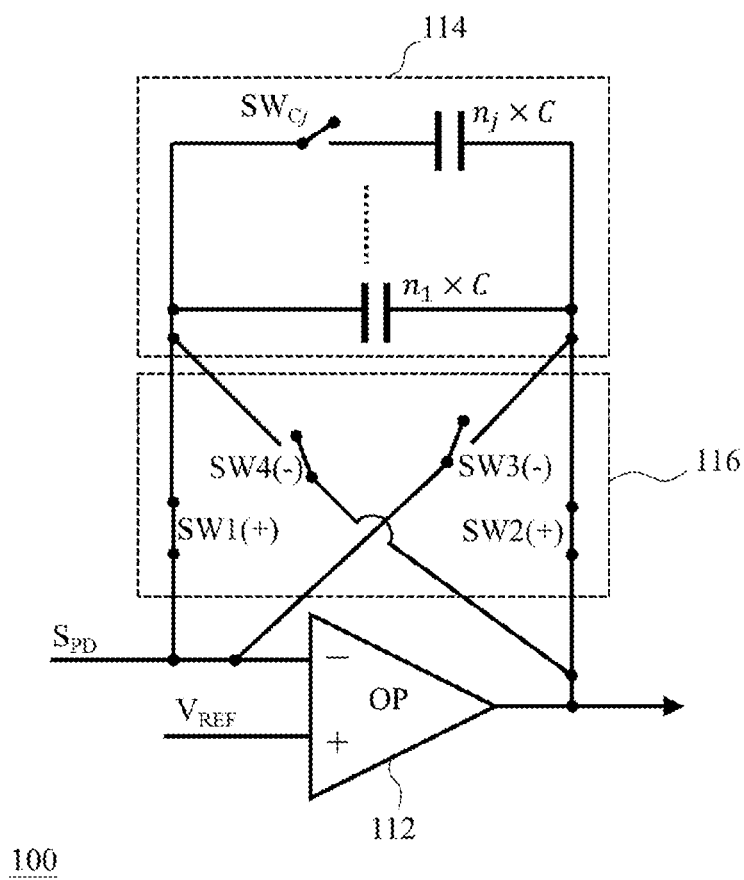

The example of FIGS. 3a~3b can be modified as shown in FIGS. 4a~4c. Referring to FIGS. 4a~4c, the capacitive path 114 includes j capacitive paths from the $1^{st}$ capacitive path (which includes a capacitor $n_1 \times C$) to the $j^{th}$ capacitive path (which includes a capacitor $n_1 \times C$), wherein each capacitive path includes a capacitor, the $j^{th}$ capacitive path further includes a $j^{th}$ capacitive-path switch $SW_{Cj}$, each of $n_1 \sim n_j$ is a scaling factor and can be determined according to the demand for implementation, C denotes a unit of capacitance, and the j is an integer greater than two. FIGS. 4a~4c show the sampling operation during three consecutive time slots (i.e., the three consecutive time slots $T_0, T_1,$ and $T_2$ in FIG. 2). Regarding the example of FIGS. 4a-4c, the ambient-light cancellation circuit 100 functions as a second-order filter and generates a filtration result $$z^0 - \frac{\sum (n_1, \ldots, n_j)}{\sum (n_1, \ldots, n_m)} z^{-1} + \frac{\sum (n_1, \ldots, n_j)}{\sum (n_1, \ldots, n_k)} z^{-2}$$

which can be scaled up/down with a known/self-developed analog/digital manner. Those having ordinary skill in the art can derive more examples from the examples of FIGS. 3a-4c.

Figure 5:
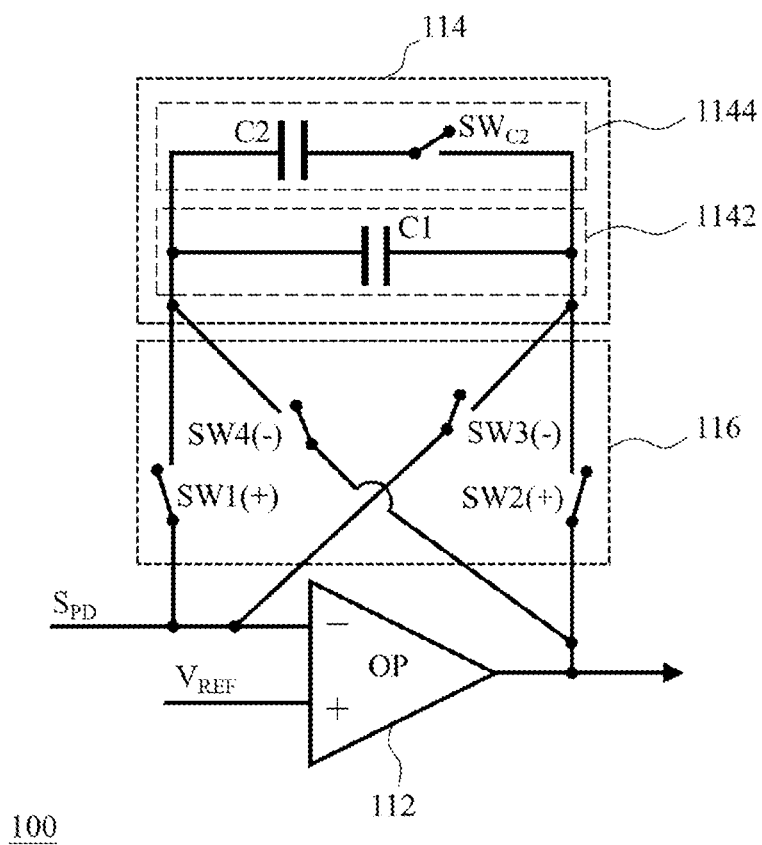
FIG. 5 shows another embodiment of the ambient light cancellation circuit of the present disclosure.
Figure 6:
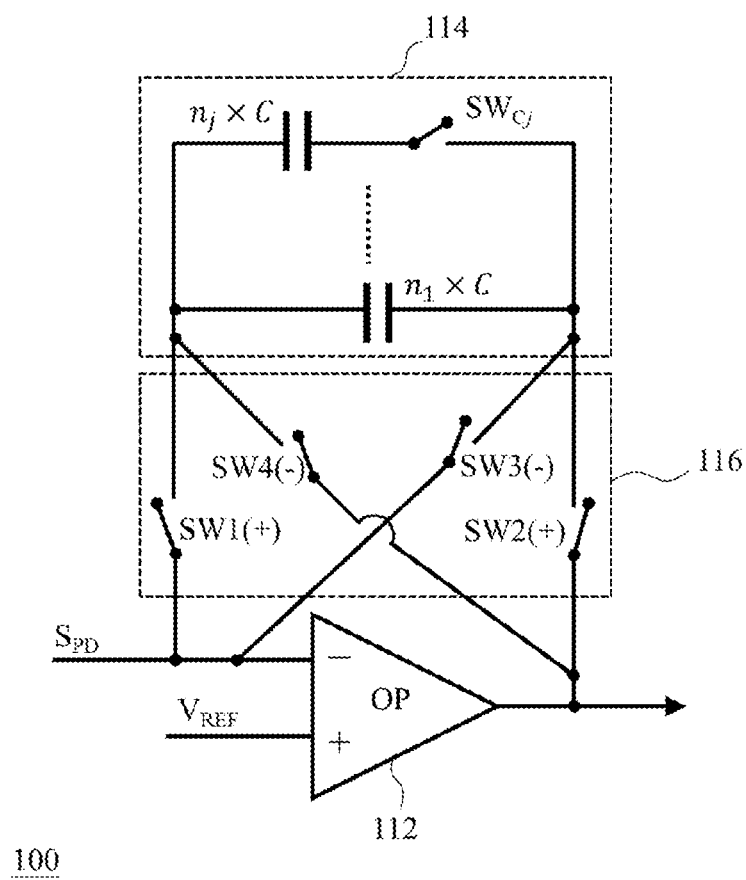
FIG. 6 shows yet another embodiment of the ambient light cancellation circuit of the present disclosure.

The embodiments of the present disclosure could be modified to include at least one of the following features:

(1) Compared with the example of FIGS. 3a~3b, the second capacitive-path switch $SW_{C2}$ is set at the other side of the second capacitor C2 as shown in FIG. 5; and compared with the example of FIGS. 4a~4c, the $j^{th}$ capacitive-path switch SW0 is set at the other side of the $j^{th}$ capacitor $n_j \times C$ as shown in FIG. 6.

(2) Compared with the example of FIGS. 3a~3b, during the even time slots $T_0$ and $T_2$ as shown in FIG. 2, the switch circuit 116 couples the amplifier 112 with the capacitor circuit 114 in a non-cross manner while the second capacitive-path switch $SW_{C2}$ is turned off; during the odd time slot $T_1$, the switch circuit 116 couples the amplifier 112 with the capacitor circuit 114 in a cross manner while the second capacitive-path switch $SW_{C2}$ is turned on; and accordingly, the ambient light cancellation circuit 100 generates a filtration result as follows: $2 \times (1z^0 - \frac{1}{2}z^{-1} + z^{-2})$.

(3) Referring to FIGS. 3a~'3b, when the switch circuit 116 couples the amplifier 112 with the capacitor circuit 114 in a non-cross manner during a certain time slot, the second capacitive-path switch $SW_{C2}$ can optionally be turned on or turned off, wherein the certain time slot is or is not one of the aforementioned N time slot(s); and when the switch circuit 116 couples the amplifier 112 with the capacitor circuit 114 in a cross manner during a certain time slot, the second capacitive-path switch $SW_{C2}$ can optionally be turned on or turned off, wherein the certain time slot is or is not one of the aforementioned M time slot(s).

(4) Referring to FIGS. 1~4c, any capacitor of the capacitor circuit 114 is a capacitor of fixed capacitance or a capacitor of adjustable capacitance. For example, the first capacitor C1 of the first capacitive path 1142 is an adjustable capacitor; and when the capacitive transimpedance amplifying circuit 110 performs sampling during each time slot, the capacitance of the adjustable capacitor can be determined according to the required filtration result.

(5) When the N is greater than one, any two of the N time slots are equal in time length (e.g., microseconds) or unequal in time length; and when the M is greater than one, any two of the M time slots are equal in time length (e.g., microseconds) or unequal in time length.

(6) Any of the N time slot(s) is equal to any of the M time slot(s) in time length (e.g., two microseconds).

Figure 7:
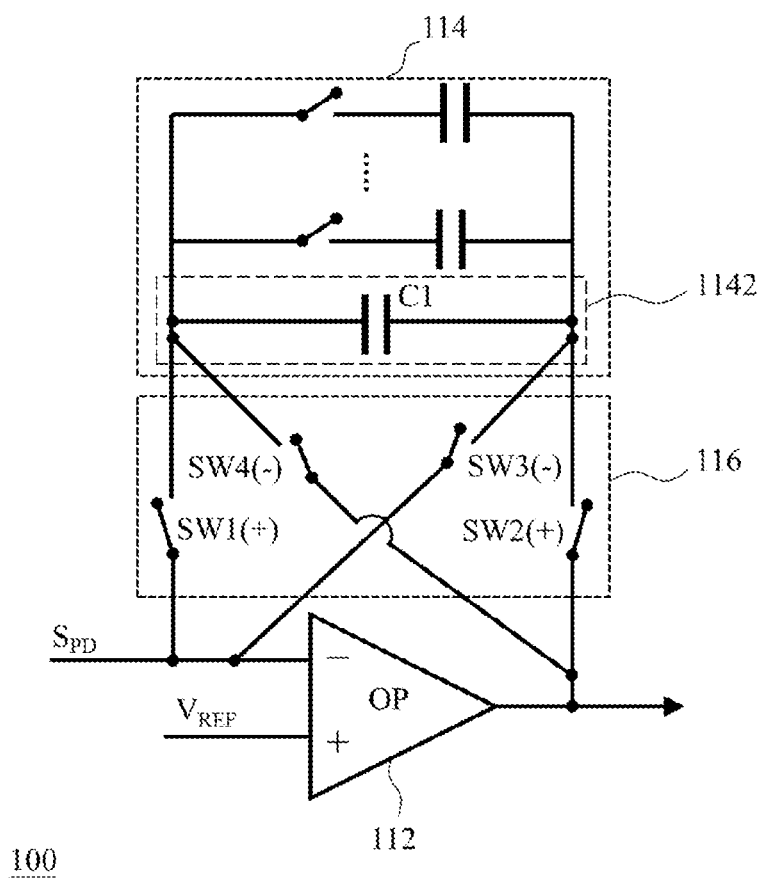
FIG. 7 shows yet another embodiment of the ambient light cancellation circuit of the present disclosure.

The example of FIGS. 3a~3b can be modified as shown in FIG. 7. As shown in FIG. 7, the capacitor circuit 114 includes a plurality of capacitive paths coupled in parallel. The plurality of capacitive paths includes the first capacitive path 1142. Each of the plurality of capacitive paths except the first capacitive path 1142 includes a switch and a capacitor, wherein the conducting state of the said switch (i.e., the switch being turned on or turned off) and the capacitance of the said capacitor are determined according to the demand for implementation to determine the filter coefficient(s) of the $K^{th}$-order filter (i.e., the ambient light cancellation circuit 100) and realize a required filtration effect.

It is noted that people having ordinary skill in the art can selectively use some or all of the features of any embodiment in this specification or selectively use some or all of the features of multiple embodiments in this specification to implement the present invention as long as such implementation is practicable; in other words, the way to implement the present invention is flexible based on the present disclosure.

To sum up, the ambient light cancellation circuit of the present disclosure functions as a multi-order filter to filter out an ambient-light signal. Compared with the prior art, the ambient light cancellation circuit of the present disclosure can be implemented flexibly to realize many kinds of filtration effects.

The aforementioned descriptions represent merely the preferred embodiments of the present invention, without any intention to limit the scope of the present invention thereto. Various equivalent changes, alterations, or modifications based on the claims of the present invention are all consequently viewed as being embraced by the scope of the present invention.

What is claimed is:

1. An ambient light cancellation circuit functioning as a $K^{th}$-order filter for sampling a detection signal (K+1) times during a sampling period and thereby filtering out an ambient-light signal of the detection signal, wherein the K is an integer greater than one, the detection signal is generated by a photoelectric device, and the ambient light cancellation circuit comprises:
 a capacitive transimpedance amplifying circuit including:
  an amplifier including an input node, an inverting input node, and an output node, wherein the input node is for receiving a reference voltage and the inverting input node is for receiving the detection signal;
 a capacitor circuit including:
  a first capacitive path including a first capacitor which includes a first electrode and a second electrode; and
 a switch circuit including:
  a first switch set between the first electrode and the inverting input node;
  a second switch set between the second electrode and the output node, wherein the first switch and the second switch are scheduled to be turned on during N time slot(s) and to be turned off during M time slot(s) so as to couple the first electrode with the inverting input node and couple the second electrode with the output node during the N time slot(s) and thereby allow the first capacitor to sample the detection signal during the N time slot(s), wherein the N time slot(s) and the M time slot(s) are included in the sampling period, each of the N and the M is a positive integer, and a sum of the N and the M is not greater than (K+1);
  a third switch set between the second electrode and the inverting input node; and
  a fourth switch set between the first electrode and the output node, wherein the third switch and the fourth switch are scheduled to be turned on during the M time slot(s) and to be turned off during the N time slot(s) so as to couple the second electrode with the inverting input node and couple the first electrode with the output node during the M time slot(s) and thereby allow the first capacitor to sample an inversion of the detection signal during the M time slot(s),
 wherein the detection signal includes a controllable-light signal and the ambient-light signal during I time slot(s); the detection signal includes the ambient-light signal without including the controllable-light signal during J time slot(s); the I time slot(s) is/are the N time slot(s) or the M time slot(s); when the I time slot(s) is/are the N time slot(s), the J time slot(s) is/are the M time slot(s); and when the I time slot(s) is/are the M time slot(s), the J time slot(s) is/are the N time slot(s).

2. The ambient light cancellation circuit of claim 1, wherein the capacitor circuit further includes:
  a second capacitive path coupled with the first capacitive path in parallel, the second capacitive path including a second capacitive-path switch and a second capacitor which includes a third electrode and a fourth electrode, one end of the second capacitive-path switch is coupled with the third electrode and another end of the second capacitive-path switch is coupled with the first electrode and the switch circuit,
  wherein the third electrode is coupled with the inverting input node through the second capacitive-path switch and the first switch, and is coupled with the output node through the second capacitive-path switch and the fourth switch; the fourth electrode is coupled with the output node through the second switch, and is coupled with the inverting input node through the third switch; and the second capacitive-path switch is scheduled to be turned on only during the N time slot(s) or the M time slot(s).

3. The ambient light cancellation circuit of claim 2, wherein a capacitance of the first capacitor and a capacitance of the second capacitor jointly determine a plurality of filter coefficients of the $K^{th}$-order filter.

4. The ambient light cancellation circuit of claim 1, wherein the capacitor circuit further includes:
  a second capacitive path coupled with the first capacitive path in parallel, the second capacitive path including a second capacitive-path switch and a second capacitor which includes a third electrode and a fourth electrode, one end of the second capacitive-path switch is coupled with the fourth electrode and another end of the second capacitive-path switch is coupled with the second electrode and the switch circuit,
  wherein the third electrode is coupled with the inverting input node through the first switch, and is coupled with the output node through the fourth switch; the fourth electrode is coupled with the output node through the second capacitive-path switch and the second switch, and is coupled with the inverting input node through the second capacitive-path switch and the third switch; and the second capacitive-path switch is scheduled to be turned on only during the N time slot(s) or the M time slot(s).

5. The ambient light cancellation circuit of claim 4, wherein a capacitance of the first capacitor and a capacitance of the second capacitor jointly determine a plurality of filter coefficients of the $K^{th}$-order filter.

6. The ambient light cancellation circuit of claim 1, wherein the capacitor circuit further includes:
  a second capacitive path coupled with the first capacitive path in parallel, the second capacitive path including a second capacitive-path switch and a second capacitor which includes a third electrode and a fourth electrode, one end of the second capacitive-path switch is coupled with the third electrode and another end of the second capacitive-path switch is coupled with the first electrode and the switch circuit,
  wherein the third electrode is coupled with the inverting input node through the second capacitive-path switch and the first switch, and is coupled with the output node through the second capacitive-path switch and the fourth switch; the fourth electrode is coupled with the output node through the second switch, and is coupled with the inverting input node through the third switch; and the second capacitive-path switch is scheduled to be turned on during X time slot(s) and turned off during Y time slot(s), the X time slot(s) and the Y time slot(s) are included in the sampling period, the X time slot(s) as a whole is different from the N time slot(s) and different from the M time slot(s), the Y time slot(s) as a whole is different from the N time slot(s) and different from the M time slot(s), and each of the X and the Y is an integer equal to or greater than zero.

7. The ambient light cancellation circuit of claim 6, wherein a capacitance of the first capacitor and a capacitance of the second capacitor jointly determine a plurality of filter coefficients of the $K^{th}$-order filter.

8. The ambient light cancellation circuit of claim 1, wherein the capacitor circuit further includes:
  a second capacitive path coupled with the first capacitive path in parallel, the second capacitive path including a second capacitive-path switch and a second capacitor which includes a third electrode and a fourth electrode, one end of the second capacitive-path switch is coupled with the fourth electrode and another end of the second capacitive-path switch is coupled with the second electrode and the switch circuit,
  wherein the third electrode is coupled with the inverting input node through the first switch, and is coupled with the output node through the fourth switch; the fourth electrode is coupled with the output node through the second capacitive-path switch and the second switch, and is coupled with the inverting input node through the second capacitive-path switch and the third switch; and the second capacitive-path switch is scheduled to be turned on during X time slot(s) and turned off during Y time slot(s), the X time slot(s) and the Y time slot(s) are included in the sampling period, the X time slot(s) as a whole is different from the N time slot(s) and different from the M time slot(s), the Y time slot(s) as a whole is different from the N time slot(s) and different from the M time slot(s), and each of the X and the Y is an integer equal to or greater than zero.

9. The ambient light cancellation circuit of claim 8, wherein a capacitance of the first capacitor and a capacitance of the second capacitor jointly determine a plurality of filter coefficients of the $K^{th}$-order filter.

10. The ambient light cancellation circuit of claim 1, wherein the capacitor circuit includes multiple capacitive paths coupled in parallel, the multiple capacitive paths include the first capacitive path, and conducting states of the multiple capacitive paths and capacitances of the multiple capacitive paths jointly determine a plurality of filter coefficients of the $K^{th}$-order filter.

11. The ambient light cancellation circuit of claim 10, wherein the sampling period includes at least (K+1) time slots in sequence; the at least (K+1) time slots include an $I^{th}$ time slot; P capacitive path(s) of the multiple capacitive paths is/are scheduled to be turned on during the $I^{th}$ time slot to sample the detection signal or the inversion of the detection signal; an equivalent capacitance of the P capacitive path(s) determines an $I^{th}$ filter coefficient of the $K^{th}$-order filter; the I is a positive integer between one and (K+1); and the P is a positive integer.

12. The ambient light cancellation circuit of claim 10, wherein capacitances of at least two of the multiple capacitive paths are equal.

13. The ambient light cancellation circuit of claim 10, wherein capacitances of at least two of the multiple capacitive paths are unequal.

14. The ambient light cancellation circuit of claim 10, wherein at least one of the multiple capacitive paths includes an adjustable capacitor.

15. The ambient light cancellation circuit of claim 1, wherein the first capacitor is an adjustable capacitor.

16. The ambient light cancellation circuit of claim 1, wherein each of the N and the M is greater than one; any two of the N time slots are equal in time length; and any two of the M time slots are equal in time length.

17. The ambient light cancellation circuit of claim 16, wherein any of the N time slots and any of the M time slots are equal in time length.

18. An ambient light cancellation circuit functioning as a $K^{th}$-order filter for sampling a detection signal (K+1) times during a sampling period and thereby filtering out an ambient-light signal of the detection signal, wherein the K is an integer, the detection signal is generated by a photoelectric device, and the ambient light cancellation circuit comprises:
  a capacitive transimpedance amplifying circuit including:
    an amplifier including an input node, an inverting input node, and an output node, wherein the input node is for receiving a reference voltage and the inverting input node is for receiving the detection signal;
    a capacitor circuit including:
      a first capacitive path including a first capacitor which includes a first electrode and a second electrode; and
      a second capacitive path coupled with the first capacitive path in parallel, the second capacitive path including a second capacitive-path switch and a second capacitor which includes a third electrode and a fourth electrode, wherein one end of the second capacitive-path switch is coupled with the third electrode and another end of the second capacitive-path switch is coupled with the first electrode; and
    a switch circuit including:
      a first switch having one end coupled with both of the first electrode and the second capacitive-path switch and having another end coupled with the inverting input node;
      a second switch having one end coupled with both of the second electrode and the fourth electrode and having another end coupled with the output node, wherein the first switch and the second switch are scheduled to be turned on during N time slot(s) and to be turned off during M time slot(s) so as to couple the first electrode with the inverting input node and couple the second electrode with the output node during the N time slot(s) and thereby allow the first capacitor to sample the detection signal during the N time slot(s), wherein the N time slot(s) and the M time slot(s) are included in the sampling period, each of the N and the M is a positive integer, and a sum of the N and the M is not greater than (K+1);
      a third switch having one end coupled with both of the second electrode and the fourth electrode and having another end coupled with the inverting input node; and
      a fourth switch having one end coupled with both of the first electrode and the second capacitive-path switch and having another end coupled with the output node, wherein the third switch and the fourth switch are scheduled to be turned on during the M time slot(s) and to be turned off during the N time slot(s) so as to couple the second electrode with the inverting input node and couple the first electrode with the output node during the M time slot(s) and thereby allow the first capacitor to sample an inversion of the detection signal during the M time slot(s),
  wherein the second capacitive-path switch is only turned on during X time slot(s) which is a part of a whole of the N time slot(s) and the M time slot(s), the X time slot(s) is the N time slot(s) or is different from the N time slot(s), and the X is a positive integer; the detection signal includes a controllable-light signal and the ambient-light signal during I time slot(s); the detection signal includes the ambient-light signal without including the controllable-light signal during J time slot(s); the I time slot(s) is/are the N time slot(s) or the M time slot(s); when the I time slot(s) is/are the N time slot(s), the J time slot(s) is/are the M time slot(s); and when the I time slot(s) is/are the M time slot(s), the J time slot(s) is/are the N time slot(s).

19. An ambient light cancellation circuit functioning as a $K^{th}$-order filter for sampling a detection signal (K+1) times during a sampling period and thereby filtering out an ambient-light signal of the detection signal, wherein the K is an integer, the detection signal is generated by a photoelectric device, and the ambient light cancellation circuit comprises:
  a capacitive transimpedance amplifying circuit including:
    an amplifier including an input node, an inverting input node, and an output node, wherein the input node is for receiving a reference voltage and the inverting input node is for receiving the detection signal;
    a capacitor circuit including:
      a first capacitive path including a first capacitor which includes a first electrode and a second electrode; and
      a second capacitive path coupled with the first capacitive path in parallel, the second capacitive path including a second capacitive-path switch and a second capacitor which includes a third electrode and a fourth electrode, wherein one end of the second capacitive-path switch is coupled with the fourth electrode and another end of the second capacitive-path switch is coupled with the second electrode; and
    a switch circuit including:
      a first switch having one end coupled with both of the first electrode and the third electrode and having another end coupled with the inverting input node;
      a second switch having one end coupled with both of the second electrode and the second capacitive-path switch and having another end coupled with the output node, wherein the first switch and the second switch are scheduled to be turned on during N time slot(s) and to be turned off during M time slot(s) so as to couple the first electrode with the inverting input node and couple the second electrode with the output node during the N time slot(s) and thereby allow the first capacitor to sample the detection signal during the N time slot(s), wherein the N time slot(s) and the M time slot(s) are included in the sampling period, each of the N and the M is a positive integer, and a sum of the N and the M is not greater than (K+1);
      a third switch having one end coupled with both of the second electrode and the second capacitive-path switch and having another end coupled with the inverting input node; and a fourth switch having one end coupled with both of the first electrode and the third electrode and having another end coupled with the output node, wherein the third switch and the fourth switch are scheduled to be turned on during the M time slot(s) and to be turned off during the N time slot(s) so as to couple the second electrode with the inverting input node and couple the first electrode with the output node during the M time slot(s) and thereby allow the first capacitor to sample an inversion of the detection signal during the M time slot(s), wherein the second capacitive-path switch is only turned on during X time slot(s) which is a part of a whole of the N time slot(s) and the M time slot(s), the X time slot(s) is the N time slot(s) or is different from the N time slot(s), and the X is a positive integer; the detection signal includes a controllable-light signal and the ambient-light signal during I time slot(s); the detection signal includes the ambient-light signal without including the controllable-light signal during J time slot(s); the I time slot(s) is/are the N time slot(s) or the M time slot(s); when the I time slot(s) is/are the N time slot(s), the J time slot(s) is/are the M time slot(s); and when the I time slot(s) is/are the M time slot(s), the J time slot(s) is/are the N time slot(s).

* * * * *